US012594176B2

(12) United States Patent
Pieper et al.

(10) Patent No.: US 12,594,176 B2
(45) Date of Patent: Apr. 7, 2026

(54) ORTHOPEDIC DEVICE AND METHOD FOR PRODUCTION

(71) Applicant: PLUS MEDICA OT GMBH, Düsseldorf (DE)

(72) Inventors: Tobias Pieper, Dortmund (DE); Alexander Hülk, Coesfeld (DE)

(73) Assignee: PLUS MEDICA OT GMBH, Düsseldorf (DE)

( * ) Notice: Subject to any disclaimer, the term of this patent is extended or adjusted under 35 U.S.C. 154(b) by 449 days.

(21) Appl. No.: 18/063,334

(22) Filed: Dec. 8, 2022

(65) Prior Publication Data

US 2023/0320880 A1     Oct. 12, 2023

(30) Foreign Application Priority Data

Dec. 13, 2021     (DE) ...................... 10 2021 006 129.2

(51) Int. Cl.
 *A61F 5/01*          (2006.01)
(52) U.S. Cl.
 CPC .............. *A61F 5/0111* (2013.01); *A61F 5/01* (2013.01); *A61F 5/0102* (2013.01)
(58) Field of Classification Search
 CPC .... A61F 5/0111; A61F 5/0102; A61F 5/0104; A61F 5/0127; A61F 5/0195; A61F 5/0106; A61F 5/0116; A61F 5/0585; A61F 5/01–34; A61G 13/123; Y10S 24/00–91
 USPC .......... 602/23, 27; 128/882; 24/68 R, 68 SK, 24/68 T
 See application file for complete search history.

(56) References Cited

U.S. PATENT DOCUMENTS

| | | | | |
|---|---|---|---|---|
| 3,296,667 A | * | 1/1967 | Streule ................... | A43C 11/14 |
| | | | | 24/578.13 |
| 6,226,844 B1 | * | 5/2001 | Lerra ................... | A44B 11/006 |
| | | | | 24/615 |
| 7,198,610 B2 | * | 4/2007 | Ingimundarson ..... | A61F 5/0123 |
| | | | | 602/26 |
| 7,785,283 B1 | | 8/2010 | Bledsoe | |
| 2009/0287127 A1 | * | 11/2009 | Hu ......................... | A61F 5/0111 |
| | | | | 602/27 |

(Continued)

FOREIGN PATENT DOCUMENTS

| | | | | |
|---|---|---|---|---|
| DE | 10 2013 019 079 A1 | 5/2015 | | |
| DE | 102020115001 A1 | * 12/2021 | ............ | A61F 5/0111 |
| WO | WO-2013156351 A1 | * 10/2013 | ........... | A61F 5/0102 |

OTHER PUBLICATIONS

Translation of DE 102020115001 (Year: 2021).*

*Primary Examiner* — Rachael E Bredefeld
*Assistant Examiner* — Seth R. Brown
(74) *Attorney, Agent, or Firm* — WCF IP

(57) ABSTRACT

The invention relates to an orthopedic device with a dimensionally stable element (2) for positioning on a body part and a strap (30) for fastening the dimensionally stable element (2) to the body part, the strap (30) being guided through a deflection eyelet (8), wherein the dimensionally stable element (2) comprises at least one fastening device (4) with a feed-through (10) with a longitudinal direction, along which a connection element (6) extends through the feed-through (10) to which the deflection eyelet (8) is attached, the connection element (6) comprising a first end (20) on which a first anchor (22) is formed in such a way that the first end (20) with the first anchor (22) cannot be pulled through the feed-through (10) along the longitudinal direction.

20 Claims, 6 Drawing Sheets

(56) References Cited

U.S. PATENT DOCUMENTS

Figure 1:
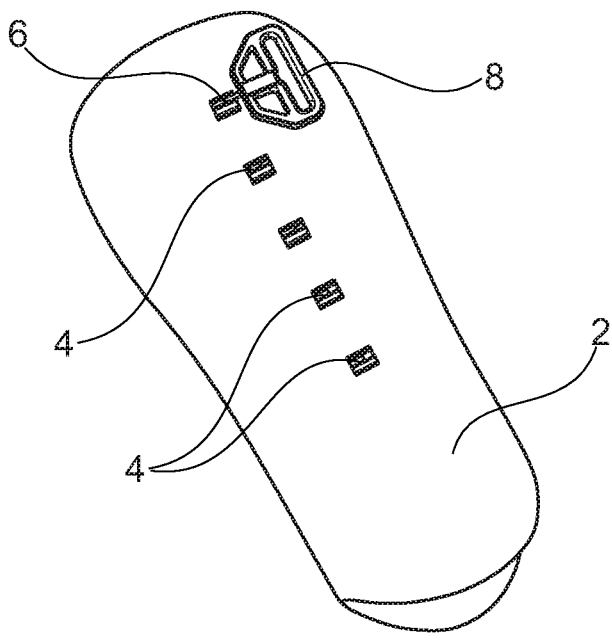

| | | |
|---|---|---|
| 2015/0150709 A1 | 6/2015 | Ljubimir et al. |
| 2015/0305912 A1 | 10/2015 | Hu et al. |

* cited by examiner

ORTHOPEDIC DEVICE AND METHOD FOR PRODUCTION

The invention relates to an orthopedic device with a dimensionally stable element for positioning on a body part and a strap for fastening the dimensionally stable element to the body part, the strap being guided through a deflection eyelet. The invention also relates to a method for producing such an orthopedic device.

Orthopedic devices are, for example, orthoses or prostheses. However, within the scope of the present invention, orthopedic devices are also understood to mean support devices that support body parts or the wearer of the device and, for example, aim to prevent or delay fatigue or exhaustion. The orthopedic device has a dimensionally stable element that is fastened to the respective body part by means of the strap. The dimensionally stable element may be a splint or a shell, for example. The dimensionally stable element may be a standard element that is not individually adjusted to the body part. Alternatively, the dimensionally stable element can also be individually adjusted for the wearer to their respective body part.

The dimensionally stable element can be made from a plastic, for example a fiber-reinforced plastic, or a metal. In the present case, a strap is understood to mean a flexible element that is preferably placed around the body part of the wearer to which the dimensionally stable element is to be fastened. The strap can be designed to be elastic or inelastic. In the context of the present invention, a deflection eyelet is any element around which the strap is placed in order to change its direction. It may be a ring, such as a D-ring or an O-ring. Loops or eyelets that are open on one side, such as those known from the lacing of hiking boots, are also considered deflection eyelets.

Corresponding orthopedic devices are known from the prior art whose dimensionally stable element is fastened to the body part of the wearer via one or multiple straps. In preferred embodiments, the strap has one end fastened to the dimensionally stable element. It is at least partially placed around the body part of the wearer and guided through the deflection eyelet. The strap is subsequently at least partially guided around the body part in the opposite direction and fixed. Here, the strap can be fixed to itself. In this case, the one side of the strap is preferably equipped with a velcro element. The opposite side of the strap features the counter element, so that the strap can be fixed to itself by closing the velcro. Alternatively or additionally, after being guided through the deflection eyelet, the end of the strap can also be fixed to a dimensionally stable element of the orthopedic device or to another component or element of the orthopedic device.

The position of the deflection eyelet in particular therefore has a significant influence on the course of the strap in the mounted state of the orthopedic device. However, a non-optimal fit and course of the strap can lead to pressure points and pain for the wearer, or at least to an uncomfortable wearing sensation. Particularly if the dimensionally stable element is a standard component which is not individually manufactured for the wearer, the optimal course of the strap cannot often be predicted in detail. Even in the case of individually produced single pieces that are used as a dimensionally stable element, this prediction is often difficult as the individual wearing sensation felt by the wearer is difficult to predict or cannot be predicted at all. However, according to the prior art, the position and the course of the strap and/or of the deflection eyelet cannot be changed following completion of the orthopedic device. Consequently, the wearer must either make do with the less than optimal fit or a new orthopedic device must be created. This is cost-intensive and time-consuming.

The invention is based on the task of eliminating or at least reducing the disadvantages of the prior art.

The invention solves the addressed task in that the dimensionally stable element comprises at least one fastening device with a feed-through with a longitudinal direction, along which the one connection element extends through the feed-through, to which the deflection eyelet is fastened, the connection element comprising a first end at which a first anchor is formed in such a way that the first end with the first anchor can be pulled through the feed-through along the longitudinal direction.

In the context of the present invention, if the connection element is removed from the feed-through, in that it is moved through the feed-through to the point that it completely leaves it, this is referred to as the connection element being "pulled" through the feed-through. This only describes the movement, but not the direction of the applied force, that is responsible for this movement. Of course, it is also possible to apply a compressive force that induces this movement of the connection element through the feed-through. In this case too, this is referred to in the present invention as the connection element being "pulled" through the feed-through.

Preferably, the connection element is nevertheless fastened to the dimensionally stable element of the orthopedic device via the fastening device such that it can be detached. The connection element is a cable, a wire or a clip, for example. The connection element exhibits a length which determines, for example, a distance of the deflection eyelet from the fastening device. It is not absolutely necessary for this distance to correspond to the length of the connection element. However, it is the case that a longer connection element also leads to a greater distance of the deflection eyelet from the fastening device.

In a preferred embodiment, the first anchor is detachably arranged on the first end of the connection element. The first anchor can be designed in the shape of a sleeve, for example, which comprises an inner thread that is designed to correspond with an outer thread, which is arranged on the first end of the connection element. This makes it especially easy to detach the first anchor from the first end of the connection element. In a preferred embodiment, the first anchor has a larger cross-section than the connection element. In this case, the diameter of the first anchor is preferably larger than the diameter of the feed-through, so that the fastening device can be moved through the feed-through and displaced within it, but it cannot be pulled through the feed-through along the longitudinal direction and thus removed from the dimensionally stable element of the orthopedic device. In this case, this is prevented by the first anchor, the cross-section or diameter of which is too large to be pulled through the feed-throughs.

If the first anchor is removed from the first end of the connection element, the connection element and the first end of the connection element can be pulled through the feed-through along the longitudinal direction, thereby separating and removing the connection element from the dimensionally stable element. As a result, it is possible, for example, to replace a connection element with another connection element of a different length or which has a different type of deflection eyelet, for example.

Alternatively or additionally, the feed-through has a section in which the first anchor can at least partially, but preferably completely, accommodated. In a preferred embodiment, this section is designed to have a larger cross-section than the remainder of the feed-through, wherein this larger cross-section preferably corresponds to the cross-section and diameter of the first anchor. In the mounted state of the orthopedic device, the strap also exerts a tensile force on the connection element via the deflection eyelet. This tensile force preferably acts in the direction in which the first anchor cannot be pulled through the feed-through. For example, to prevent a detachable anchor from becoming inadvertently detached from the first end of the connection element, it can be accommodated in the section of the feed-through. It can also be advantageous from an aesthetic and visual perspective to arrange the first anchor in the section of the feed-through, thereby removing it from the user's field of vision.

In a preferred embodiment, the feed-through comprises a slit, the width of which is greater than the diameter of the connection element and smaller than the diameter of the anchor. The slit preferably extends over the entire longitudinal direction of the feed-through. In this configuration, if a tensile force is exerted on the connection element, as the strap does, for example, when the orthopedic device is in the mounted state, the connection element moves as a consequence of this force as far as possible through the feed-through. This movement ends when the first anchor cannot be moved any further through the feed-through because it rests with its face against a corresponding face of the fastening device. Preferably, the first anchor is then located in the section of the feed-through in which it can be accommodated. In this position, the connection element, at whose first end the first anchor is located, cannot be removed from the feed-through. The connection element cannot be pulled through the feed-through along the longitudinal direction of the feed-through, as this is prevented by the first anchor. Moreover, the connection element cannot be removed through the slit of the feed-through, as its width is indeed greater than the diameter of the connection element, but the width is too small to move the first anchor located in the feed-through through the slit.

However, with this configuration it is not necessary to remove the first anchor from the first end of the connection element in order to remove the connection element from the dimensionally stable element of the body part. Rather, it is enough to move the connection element so far along the longitudinal direction through the feed-through that the first anchor is no longer accommodated in a section of the feed-through. In this state, only the connection element extends through the feed-through. Its diameter is smaller than the width of the slit, so that the connection element cannot be removed from the feed-through along the longitudinal direction, but it can leave it through the slit of the feed-through. In this configuration, it is therefore possible, even with a non-detachable first anchor, to remove the connection element from the feed-through and thus from the dimensionally stable element of the orthopedic device.

The connection element preferably has a second end at which a second anchor is formed. The second end is preferably arranged opposite the first end.

In a preferred embodiment, the fastening device features a second feed-through with a longitudinal direction, along which the connection element extends, the second anchor being designed in such a way that the second end with the second anchor cannot be pulled through the feed-through along the longitudinal direction. The embodiment of the second feed-through preferably corresponds to the embodiment of the first feed-through.

In this embodiment, the connection element consequently extends with both ends through one of the two feed-throughs, respectively. This forms a loop to which the deflection eyelet is attached or can be attached. The deflection eyelet can feature a channel, for example, through which the connection element is guided. The two feed-throughs of the fastening device preferably do not run parallel to each other; rather, they extend towards each other. In this case, the two anchors are preferably arranged on the same side of the two feed-throughs. In another embodiment, a segment of the connection element forms the deflection eyelet. This refers to a part of the connection element that is arranged between the two ends and, in this case, comes into direct contact with the strap.

In this embodiment, to remove the connection element from the dimensionally stable element of the orthopedic device, it is advantageous if both the first anchor and the second anchor are arranged at their respective end of the connection element such that they can be detached. In this case, both the first anchor and the second anchor can be removed. The first end of the connection element can then be pulled through the first feed-through. Following the removal of the second anchor, the second end can be pulled through the second feed-through along the longitudinal direction. The connection element is then no longer connected to the fastening device and can be replaced, for example. An advantage of this embodiment is the fact that the deflection eyelet does not have to be removed or detached from the connection element.

Preferably, the deflection eyelet is arranged on the connection element such that it can be detached. In an especially preferred embodiment, the deflection element is arranged on the connection element in such a way that it can be detached from the connection element when the connection element extends through both feed-throughs of the fastening device. In this case, if only the type or size of the deflection eyelet is to be changed, rather than the connection element, such that the deflection element is replaced, this can be achieved without having to remove the connection element from the dimensionally stable element of the orthopedic device.

In this embodiment, in order to be able to replace the connection element, the connection element has to be removed from the dimensionally stable element of the orthopedic device. For this purpose, it is enough to remove one of the two anchors from its respective end. The respective end can then be pulled through the corresponding feed-through. In this state, the deflection eyelet can then be removed from the connection element and the connection element can then be pulled through the respective other feed-through. In this case, it is not necessary to remove the respective other anchor, as the connection element is pulled through the respective feed-through in the opposite direction to the direction in which a tensile force is exerted in the mounted state of the orthopedic device.

The second feed-through preferably comprises a slit, the width of which is greater than the diameter of the connection element and smaller than the diameter of the second anchor. Preferably, the second feed-through also has a section in which the second anchor can at least partially, but preferably completely, accommodated. When a tensile force is exerted on the connection element, the second anchor is moved into this section of the second feed-through and preferably entirely accommodated there. In this position, it is not possible to remove the connection element from the second feed-through. The connection element cannot be pulled out of the second feed-through along its longitudinal direction, as the cross-section of the second anchor does not allow it to pass through the second feed-through. The connection element can also not be removed through the slit of the second feed-through, as its width is not sufficient to allow the second anchor to pass through. Only when the connection element is moved in the opposite direction and the second anchor is removed from the section of the second feed-through can the connection element be moved through the slit of the second feed-through and thus removed from the fastening device and therefore from the dimensionally stable element of the orthopedic device.

In a preferred embodiment, the deflection eyelet is attached to the second anchor, the second anchor preferably being identical to the first anchor. In this embodiment, the second end of the connection element, where the second anchor is located, is preferably not inserted into a second feed-through of the fastening device or guided through it, but is connected to the deflection eyelet. The connection element then does not form a loop, but connects the fastening device to the deflection eyelet.

The deflection eyelet preferably features an eyelet feed-through, through which the connection element is guided, the eyelet feed-through preferably comprising a section in which the second anchor can preferably be completely, but at least partially, accommodated. Here, the second anchor and the eyelet feed-through are designed in such a way that the second end with the second anchor cannot be pulled through the eyelet feed-through along its longitudinal direction.

The eyelet feed-through preferably comprises a slit, the width of which is greater than the diameter of the connection element and smaller than the diameter of the second anchor. The eyelet feed-through then acts like the first feed-through and/or the second feed-through if these have a corresponding slit.

Preferably, the dimensionally stable element has multiple fastening devices. They are arranged at different points on the dimensionally stable element or, where applicable, the multiple dimensionally stable elements of the orthopedic device. The orthopedic device preferably comprises fewer straps and fewer deflection eyelets, and thus preferably also fewer connection elements than fastening devices. Since the connection element, via which the deflection eyelet is connected to the dimensionally stable element of the orthopedic device, can be removed and disassembled from the fastening device, it is possible to select the fastening device on which the connection element is arranged and to change it after assembly. It is therefore possible to respond to individual requirements of the wearer of the orthopedic device, so as to achieve the most pleasant wearing sensation possible. In addition, the orthopedic technician can also select the position that optimizes the effect of the device and try out multiple positions on the patient, for example.

Preferably, the fastening devices are arranged equidistantly to each other. Particularly preferably, the first feed-throughs and/or second feed-throughs, where provided, of the various fastening devices extend parallel to each other.

In a preferred embodiment of the orthopedic device, the dimensionally stable element and at least one of the fastening devices, but preferably all fastening devices, are produced in an additive manufacturing process, such as a 3D printing process. If the dimensionally stable element of the orthopedic device only features one fastening device, it is preferably designed as a single piece with the rest of the dimensionally stable element. For particular applications, it may be advantageous to produce at least one fastening device together with the rest of the dimensionally stable element in the additive manufacturing process and to design at least one fastening device as a separate component. The latter can be glued, welded or otherwise detachably connected to the rest of the dimensionally stable element. Even in the case of orthopedic devices produced in an additive manufacturing process, which can be customized with little effort, it has surprisingly been proven beneficial to provide multiple fastening devices instead of defining an optimal position in advance. The adjustment on the patient is decisive in determining the optimum position.

The orthopedic device is preferably an ankle orthosis with a lower leg section and a foot section. The lower leg section is designed to be mounted on the wearer's lower leg. It has preferably been individually adjusted to fit the wearer. The foot section is designed to be mounted on the wearer's foot. It has preferably been individually adjusted to fit the wearer. The foot part and the lower leg part are preferably hinged together. In this form, the orthopedic device preferably has multiple fastening devices that are arranged along the longitudinal extension of the lower leg section.

Preferably, the foot part features a dimensionally stable part on which a fastening device is located. The latter is situated at the lateral side in the heel area of the foot section. It is difficult to arrange a standard fastener known from the prior art at this point because the strap and/or its fastener and/or the deflection eyelet then rests on the wearer's ankle. Given that the strap and therefore also the deflection eyelet and its fastener, for example the connection element, are subjected to a tensile force in the mounted state, this force is then transferred to the ankle and leads to an unpleasant wearing sensation at the very least; in the worst case, it leads to pressure points and pain. With this embodiment of the invention, it is therefore advantageous to arrange the fastening devices distally of the ankle in the ankle area of the foot section, wherein the first feed-through and/or the second feed-through extends at an angle of at least 35°, preferably at least 40° and at most 55°, preferably at most 50°, especially preferably at an angle of 45° to the contact surface of the foot section, particularly to the ground the wearer of the orthosis is standing on, when the orthosis is in the mounted state. By having a flexible connection element, the course of the tensile force generated and transferred by the strap can be controlled. Particularly preferably, the first feed-through and/or the second feed-through extends from one area behind the ankle to an area in front of the ankle. The first feed-through and/or the second feed-through may denote a curve and therefore do not have to be designed as straight lines. This applies to all embodiments described here.

In addition, the joint of the orthopedic device is often located in the ankle area, so that the connection element does not run over this area, it can be guided past it by a channel guide. The deflection eyelet can thus be brought into the optimal position without the fastening device having to be at the same point. This is particularly advantageous because the desired position on the top of the ankle orthosis often needs to be reworked by the orthopedic technician. If a fastening device were located in this area, the possibilities for reworking would be considerably limited. Therefore, a further advantage of the present invention is that the position of the fastening device on the dimensionally stable element and the position of the deflection eyelet are decoupled from one another. This makes it possible to create an orthopedic device that builds up less and is therefore better to wear under clothing.

The invention also solves the addressed task by way of a method for producing an orthopedic device of the type described here in which at least the dimensionally stable element with at least one fastening device, preferably with all fastening devices, are produced in an additive manufacturing process, wherein the number and/or the position and/or the orientation of the fastening devices are taken into account as input parameters.

To produce the dimensionally stable element with the fastening device or fastening devices in an additive manufacturing process, for example a 3D printing process, input parameters are preferably requested from a user of a corresponding manufacturing device, for example a 3D printer. To this end, the manufacturing device preferably comprises an input device, for example a graphic user interface, so that input parameters can be entered into and transmitted to an electrical control unit that is responsible for controlling the manufacturing device. The parameters include, for example, the number of fastening devices to be produced in the additive manufacturing process. Additionally or alternatively, the parameters include the position and/or orientation of the fastening devices. The parameters can be stored in an electronic data memory which can be accessed by the electrical control unit that controls the manufacturing device. Alternatively or additionally, they are entered by the input device.

The position and/or orientation of a fastening device can be individually set by a user of the manufacturing device, for example. Alternatively, only areas of the dimensionally stable element to be produced can be specified in which a certain number of fastening devices, which can be individually selected or specified, are arranged. Preferably, parameters of the arrangement can be predetermined, making it possible, for example, to select whether the fastening devices are arranged equidistantly and/or parallel to each other.

In the following, a number of embodiment examples of the invention will be explained in more detail with the aid of the accompanying figures.

They show

Figure 3:
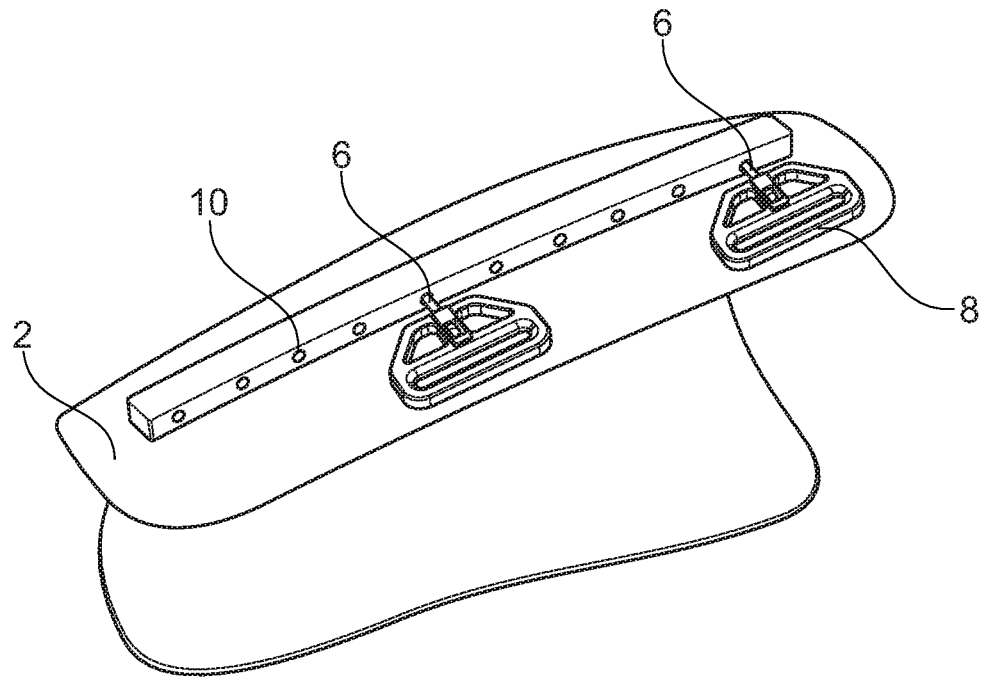
Figure 4:
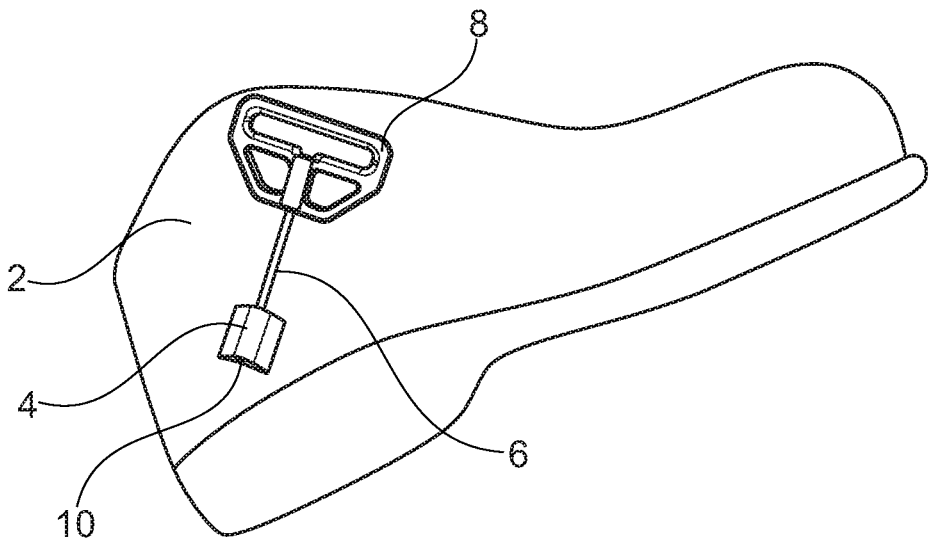
Figures 5, 6, 7, 8, 9, 10:
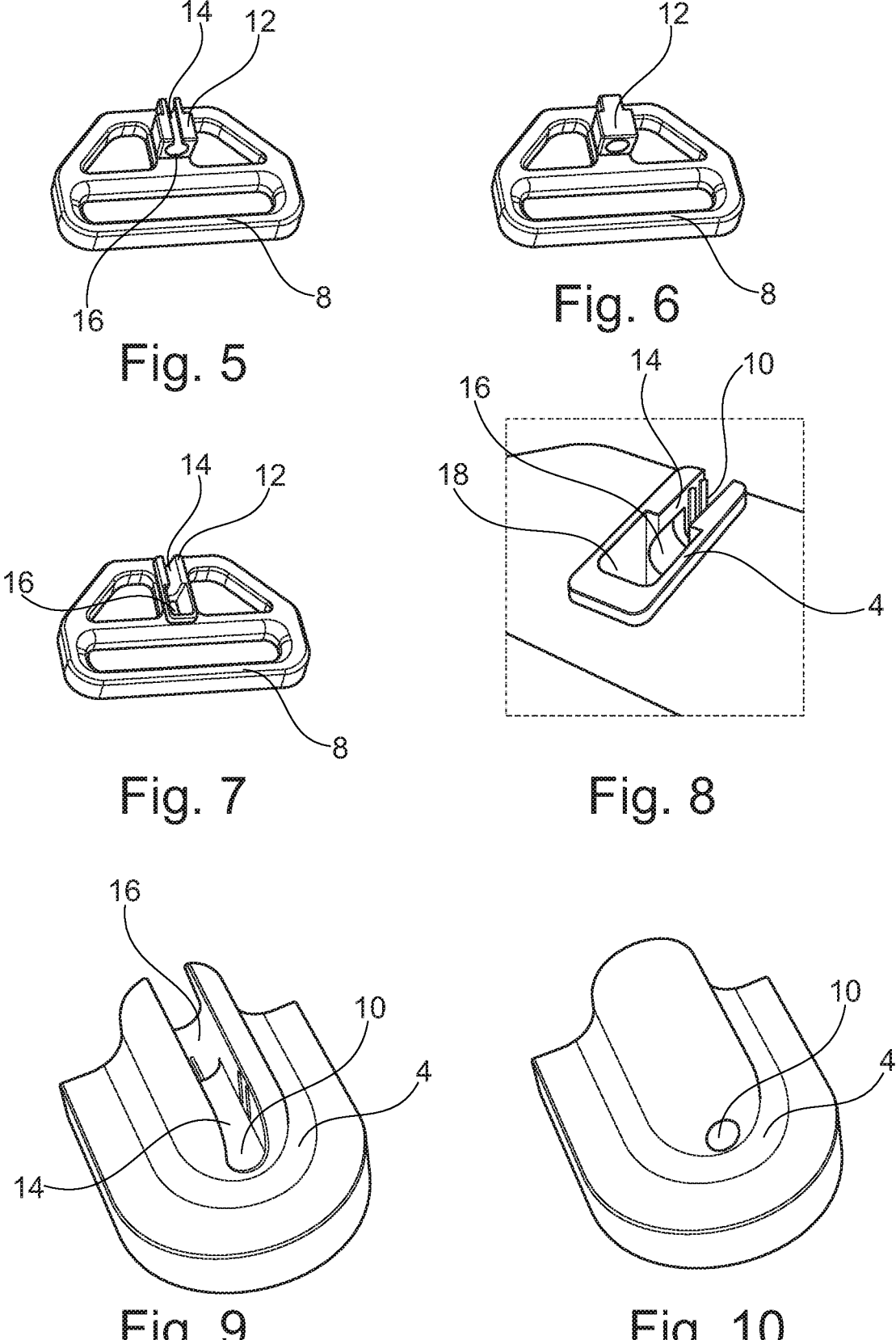
Figure 11:
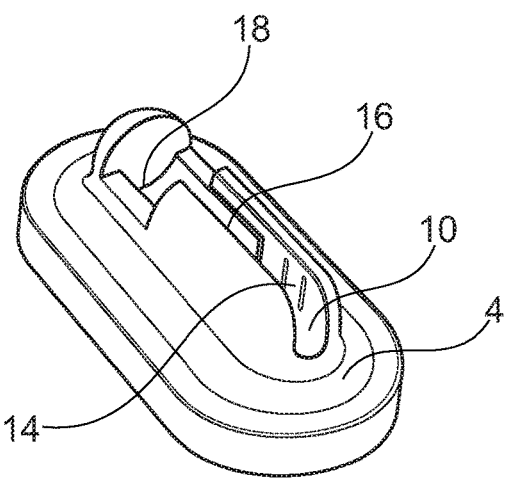
Figures 12, 13, 14:
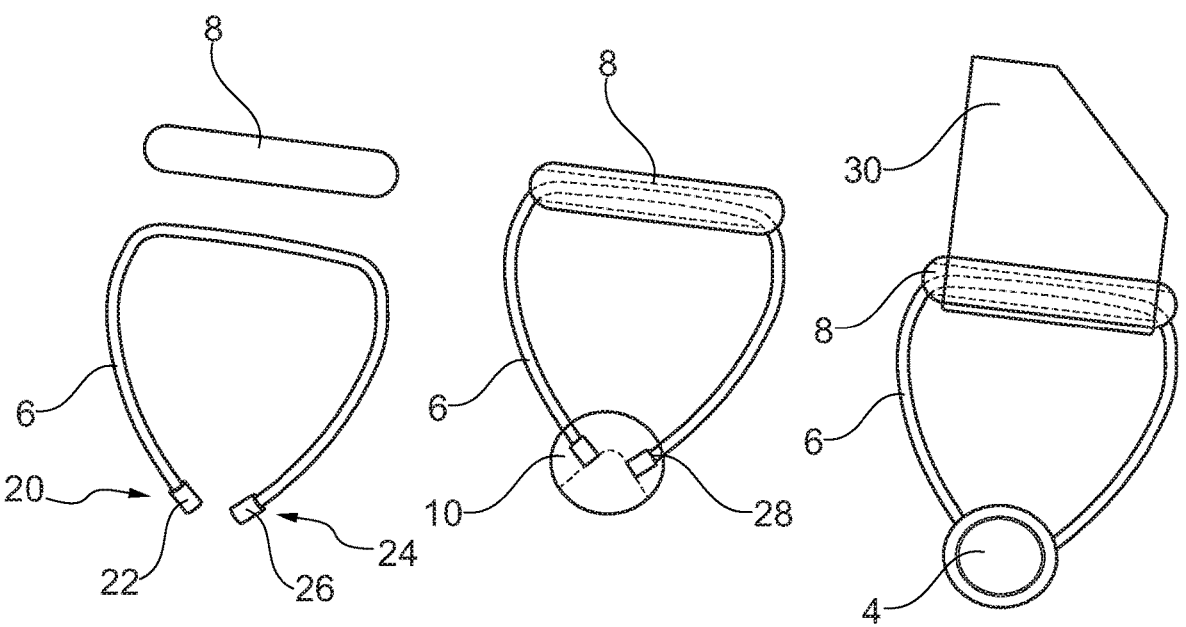
Figures 15, 16:
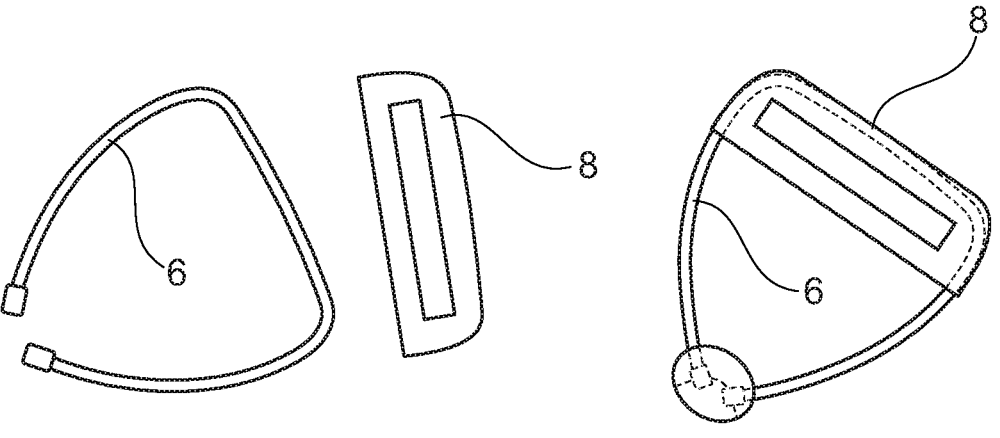
Figure 17:
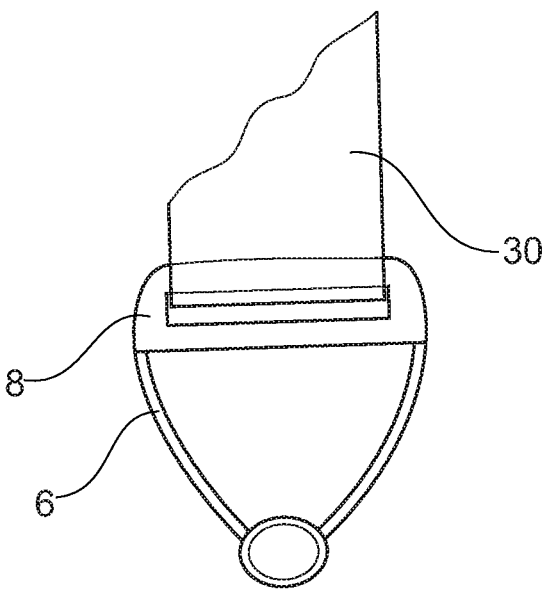
Figure 18:
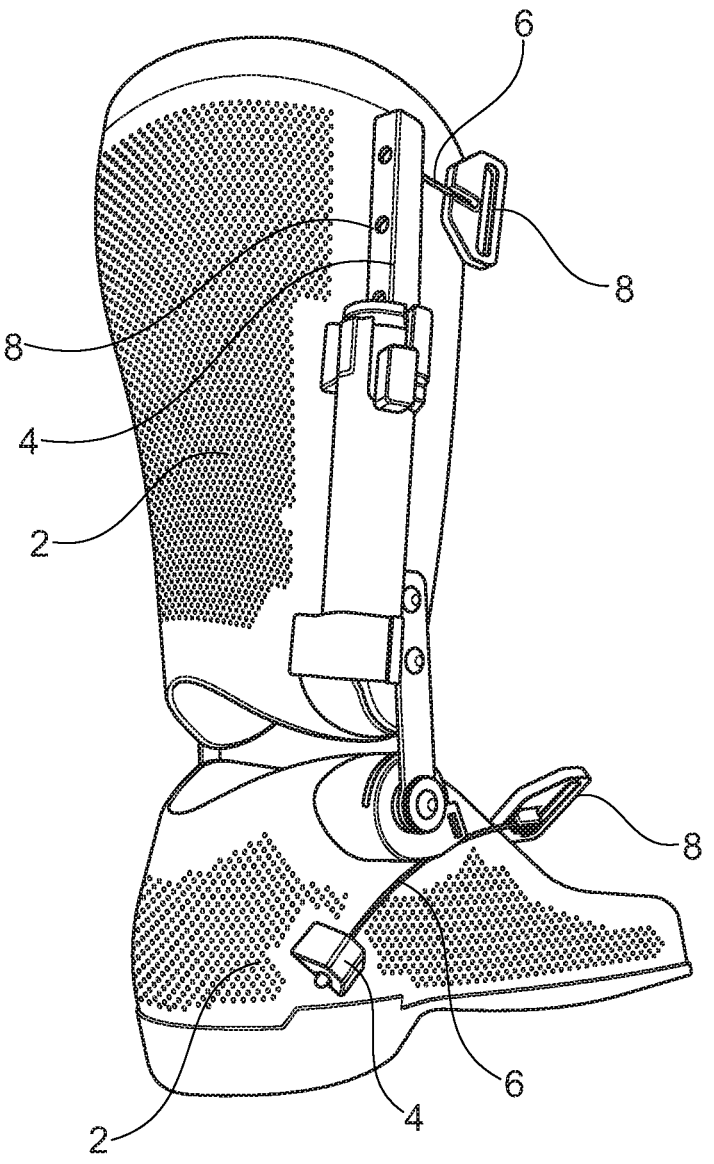

FIGS. 1 to 4—schematic representations of a dimensionally stable element with at least one fastening device, FIGS. 5 to 7 schematic representations of various deflection eyelets, FIGS. 8 to 11 schematic representations of various fastening devices, FIGS. 12 to 14—schematic representations of different elements according to further embodiment example of the present invention, FIGS. 15 to 17—schematic representations of different elements according to further embodiment example of the present invention and FIG. 18—a representation of an orthopedic device according to a further embodiment of the present invention.

FIG. 1 depicts a dimensionally stable element 2 of an orthopedic device according to a first embodiment example of the present invention. It is a lower leg shell that is used, for example, for an ankle orthosis and can be arranged on a lower leg of a wearer of the orthosis. The dimensionally stable element 2 features multiple fastening devices 4, which protrude outwards from the base body of the dimensionally stable element 2. The shape and configuration of the fastening devices 4 are described in more detail below. A deflection eyelet 8 is arranged on the top fastening device 4 via a connection element 6, which is designed in the shape of a very short cord.

Figure 2:
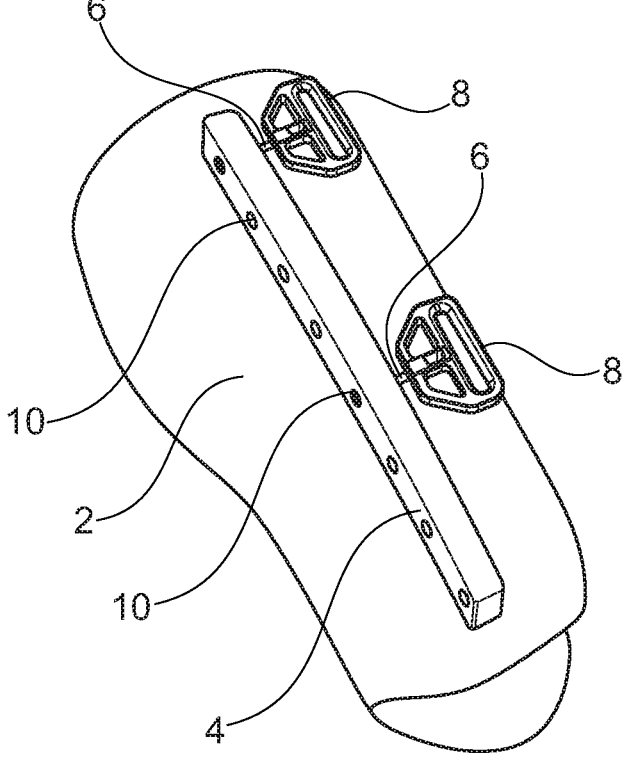

FIG. 2 shows a dimensionally stable element 2, which also comprises a plurality of fastening devices 4. These are designed as a single element. Each fastening device 4 has a feed-through 10, the feed-throughs 10 and thus the fastening devices 4 being arranged equidistantly in the embodiment example shown. In FIG. 2 there are two deflection eyelets 8, each of which is connected to the fastening devices 4 via a connection element 6. Each of the connection elements 6 extends through a feed-through 10, which is, however, only schematically indicated in FIG. 2.

FIG. 3 shows the dimensionally stable element 2 from FIG. 2 from a different perspective. In FIG. 3, it is clear that the two connection elements 6, by each of which one of the two deflection eyelets 8 is attached, extend into one of the feed-throughs 10.

FIG. 4 shows a different configuration. Here, the dimensionally stable element 2 is part of a foot section of an ankle orthosis. The deflection eyelet 8 is connected via the connection element 6 to a fastening device 4, which comprises a feed-through 10 through which the connection element 6 passes.

FIGS. 5 to 7 each show a deflection eyelet 8 through which a strap can be guided and deflected. Each of the deflection eyelets 8 exhibit an eyelet feed-through 12, which is designed differently in each of the FIGS. 5 to 7. In FIG. 5, the eyelet feed-through 12 features a slit 14 which, the embodiment example shown, extends across the entire longitudinal extension of the eyelet feed-through 12. The slit 14 has a width that is greater than a diameter of a connection element 6 that can be guided through the eyelet feed-through 12. At the lower end of the eyelet feed-through 12 in FIG. 5 is a section 16 that exhibits a larger diameter than the rest of the eyelet feed-through 12. In FIG. 5, a connection element 6, which has an anchor at its end and is guided through the eyelet feed-through 12, can be displaced upwards until the anchor is partially, but preferably completely, accommodated in this section 16. From this point onwards, it is not possible to pull the connection element 6 further in this direction through the eyelet feed-through 12.

FIG. 6 shows a similar shape, which only differs from the shape of eyelet feed-through 12 shown in FIG. 5 in that it does not have a slit. FIG. 7, on the other hand, depicts an eyelet feed-through 12 in which the section 16 can be clearly seen. The eyelet feed-through 12 in FIG. 7 also features the slit 14 and as such is open at the top. The slit 14 also has a greater width in the section 16, which has a larger cross-section in comparison to the rest of the eyelet feed-through 12. A connection element 6, at the end of which an anchor is located, can therefore be inserted from above through the slit 14 into the eyelet feed-through 12. Only when a tensile force acts on the connection element 6 is it no longer possible, due to the resulting friction, to remove connection elements 6 from the eyelet feed-through 12.

FIGS. 8 to 11 depict different embodiments of a fastening device 4. FIG. 8 shows a first configuration in which the feed-through 10 features a slit 14, i.e. it is designed to be open at the top. A section 16 can be seen inside the feed-through 10, the former having a larger cross-section than the rest of the feed-through 10. This section is configured to completely accommodate an anchor, which is located at an end of a connection element 6. In order to be able to position this anchor in the section 16, the fastening device 4 has an insertion opening 18, the dimensions of which are such that the anchor can be completely accommodated.

FIG. 9 shows a fastening device 4 in which the feed-through 10 has the slit discussed above. It is possible to see the section 16 with the larger cross-section at the rear of the fastening device 4 in FIG. 9. The fastening device 4 shown in FIG. 10 differs from the fastening device 4 in FIG. 9 in that the feed-through 10 does not feature a slit.

FIG. 11 shows a fastening device 4 which is very similar in function and design to the fastening device 4 shown in FIG. 8. It is designed merely as a raised element and is consequently placed on a base body of a dimensionally stable element.

The feed-through 10 features the slit 14 and the insertion opening 18 is shown in the rear region, through which an anchor can be inserted into the fastening device 4 and then into the section 16.

FIGS. 12 to 14 schematically depict a different embodiment. FIG. 12 first shows a connection element 6 that has a first end 20 with a first anchor 22 and a second end 24 with a second anchor 26. FIG. 12 also shows another form of the deflection eyelet 8, which is in the form of a hose. The two ends 20, 24 of the connection element 6 are arranged to interact with a fastening device 4.

This is shown in FIG. 13. The connection element 6 extends through the deflection eyelet 8, which is shown by the dashed lines. The two ends 20, 24 of the connection element 6 are inserted into a first feed-through 10 and into a second feed-through 28, so that the connection element 6 forms a loop. FIG. 14 shows the situation in a schematic top view. The ends 20, 24 of the connection element 6 are arranged in the fastening device 4 and cannot be seen. A strap 30 is placed around the deflection eyelet 8.

FIGS. 15 to 17 show a slightly different embodiment, which differs from the embodiment in FIGS. 12 to 14 in particular in that the deflection eyelet 8 not only includes the tunnel through which the connection element 6 is guided, but itself forms an eyelet through which the strap 30 is guided.

FIG. 18 shows an orthopedic device in the form of an ankle orthosis. It has a first dimensionally stable element 2 in the form of a foot section, which is arranged on a foot of a wearer of the orthopedic device. It also has a second dimensionally stable element 2 in the form of a lower leg section, which can be mounted on a lower leg of the wearer. Both dimensionally stable elements 2 each have at least one fastening device 4, each of which has a feed-through 10. A connection element 6 is or can be guided through said feed-through. A deflection eyelet 8 is arranged on each of the depicted connection elements 6.

REFERENCE LIST 2 dimensionally stable element
4 fastening device
6 connection element
8 deflection eyelet
10 feed-through
12 eyelet feed-through
14 slit
16 section
18 insertion opening
20 first end
22 first anchor
24 second end
26 second anchor
28 second feed-through
30 strap

The invention claimed is:

1. An orthopedic device, comprising:
a dimensionally stable element for positioning on a body part;
wherein the dimensionally stable element comprises
at least one fastening device with a feed-through with a longitudinal direction, a flexible connection element which extends through the feed-through, wherein the connection element comprises a first end on which a first anchor is arranged such that the first end with the first anchor cannot be pulled through the feed-through along the longitudinal direction, wherein the connection element comprises a second end on which a second anchor is arranged, wherein the connection element is a wire or cable, and
a deflection eyelet connected or connectable to the connection element; and
a strap for fastening the dimensionally stable element to the body part, wherein the strap is guidable through the deflection eyelet.

2. The orthopedic device according to claim 1, wherein the first anchor is detachably arranged on the first end of the connection element.

3. The orthopedic device according to claim 1, wherein the feed-through comprises a section in which the first anchor is partially or completely accommodatable.

4. The orthopedic device according to claim 3, wherein the feed-through comprises a slit which has a width which is greater than a diameter of the connection element, but where the width is smaller than a diameter of the first anchor.

5. The orthopedic device according to claim 1, wherein the at least one fastening device comprises a second feed-through with a longitudinal direction along which the connection element extends, and wherein the second anchor is designed such that the second end with the second anchor cannot be pulled through the feed-through along the longitudinal direction of the second feed-through.

6. The orthopedic device according to claim 5, wherein the second feed-through comprises a slit which has a width which is greater than a diameter of the connection element, but where the width is smaller than a diameter of the second anchor.

7. The orthopedic device according to claim 1 wherein the deflection eyelet is attached or attachable to the second anchor.

8. The orthopedic device according to claim 7, wherein the deflection eyelet comprises an eyelet feed-through through which the connection element is guidable.

9. The orthopedic device according to claim 8, wherein the eyelet feed-through comprises a slit which has a width which is greater than a diameter of the connection element, but where the width is smaller than a diameter of the second anchor.

10. The orthopedic device according to claim 1, wherein the dimensionally stable element comprises multiple fastening devices.

11. The orthopedic device according to claim 10, wherein the multiple fastening devices are arranged equidistantly to each other.

12. The orthopedic device according to claim 10, wherein the dimensionally stable element and at least one fastening device of the multiple fastening devices are produced in an additive manufacturing process.

13. The orthopedic device according to claim 10 wherein the orthopedic device is configured as an ankle orthosis with a lower leg section and a foot section.

14. A method for producing the orthopedic device according to claim 1 wherein at least the dimensionally stable element with at least one fastening device is produced in an additive manufacturing process, wherein a number and/or a position and/or an orientation of the at least one fastening device is taken into account as input parameters.

15. The orthopedic device according to claim 1 wherein the first anchor and the second anchor are substantially identical.

16. The orthopedic device according to claim 8 wherein the eyelet feed through comprises a section in which the second anchor is partially or completely accommodatable.

17. The orthopedic device according to claim 13 wherein at least some of the multiple fastening devices are arranged along a longitudinal extension of the lower leg section.

18. The method of claim 14 wherein the at least one fastening device comprises multiple fastening devices and wherein a number of the multiple fastening devices is taken into account as an input parameter.

19. The orthopedic device of claim 1 wherein the deflection eyelet is detachably connected to the connection element.

20. An orthopedic device, comprising:
a dimensionally stable element for positioning on a body part;
wherein the dimensionally stable element comprises at least one fastening device with a feed-through with a longitudinal direction,
a flexible connection element which extends through the feed-through, wherein the connection element comprises a first end on which a first anchor is arranged such that the first end with the first anchor cannot be pulled through the feed-through along the longitudinal direction, wherein the connection element comprises a second end on which a second anchor is arranged, and
a deflection eyelet connected or connectable to the connection element, wherein the deflection eyelet is attached or attachable to the second anchor, wherein the deflection eyelet comprises an eyelet feed-through through which the connection element is guidable; and
a strap for fastening the dimensionally stable element to the body part,
wherein the strap is guidable through the deflection eyelet.

* * * * *